(12) United States Patent
Hutchenson et al.

(10) Patent No.: US 8,841,484 B2
(45) Date of Patent: Sep. 23, 2014

(54) PARTIALLY FLUORINATED UREAS AND AMIDES

(75) Inventors: Keith W. Hutchenson, Lincoln University, PA (US); Anilkumar Raghavanpillai, Wilmington, DE (US); Stefan Reinartz, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 316 days.

(21) Appl. No.: 13/236,786

(22) Filed: Sep. 20, 2011

(65) Prior Publication Data

US 2012/0009840 A1  Jan. 12, 2012

Related U.S. Application Data

(62) Division of application No. 11/837,653, filed on Aug. 13, 2007, now Pat. No. 8,044,239.

(51) Int. Cl.
| | |
|---|---|
| *C07C 275/28* | (2006.01) |
| *C07C 275/08* | (2006.01) |
| *C07C 323/44* | (2006.01) |
| *B32B 5/02* | (2006.01) |
| *C09D 5/16* | (2006.01) |
| *C09K 3/18* | (2006.01) |
| *C07C 233/13* | (2006.01) |
| *C07C 275/16* | (2006.01) |
| *C07C 323/41* | (2006.01) |

(52) U.S. Cl.
CPC ............... *C09K 3/18* (2013.01); *C09C 275/28* (2013.01); *C09D 5/1662* (2013.01); *C07C 275/08* (2013.01); *C07C 323/44* (2013.01); *C07C 233/13* (2013.01); *C07C 275/16* (2013.01); *C07C 323/41* (2013.01)
USPC ............ 564/160; 564/154; 106/2; 428/316.6; 428/537.1; 428/689; 428/702; 428/703; 442/153; 442/164; 442/168; 442/170; 442/180

(58) Field of Classification Search
USPC ......... 564/154, 160; 106/2; 428/316.6, 537.1, 428/689, 702, 703; 442/153, 164, 168, 170, 442/180
See application file for complete search history.

(56) References Cited

U.S. PATENT DOCUMENTS

| | | | |
|---|---|---|---|
| 3,253,978 A | 5/1966 | Bodendorf et al. |
| 3,338,825 A | 8/1967 | Taggart |
| 5,885,909 A | 3/1999 | Rudisill et al. |
| 6,413,070 B1 | 7/2002 | Meyering et al. |
| 6,420,466 B1 | 7/2002 | Haubennestel et al. |
| 6,548,431 B1 | 4/2003 | Bansal et al. |
| 6,797,655 B2 | 9/2004 | Rudisill |
| 6,831,025 B2 | 12/2004 | Rudisill |
| 2004/0038014 A1 | 2/2004 | Schaefer et al. |

FOREIGN PATENT DOCUMENTS

| | | | |
|---|---|---|---|
| JP | 08259501 | * 10/1996 |
| WO | 0035998 | 6/2000 |
| WO | 03008095 | 1/2003 |

OTHER PUBLICATIONS

Honda et al., "Molecular Aggregation Structure and Surface Properties of Poly(fluoroalkyl acrylate) Thin Films", Macromolecules, 2005, 38, pp. 5699-5705.
Trabelsi et al. "Synthese des 2-F-alkylethylamines: optimisation de l'obtention des azotures de 2-F-alkylethyle et de leur reduction en amines", Journal of Fluorine Chemistry, 69, 1994, pp. 1157-117.
Rondestvedt, Jr., et al., "Nucleophilic Displacements on B-(Perfluoroalkyl)ethyl Iodides. Synthesis of Acrylates Containing Heteroatoms", J. Org. Chem., vol. 42, No. 16, 1977, pp. 2680-2683.
Adamson, "Physical Chemistry of Surfaces", 4th Edition, John Wiley & Sons, 1982, pp. 338-361.

* cited by examiner

*Primary Examiner* — Shailendra Kumar

(57) ABSTRACT

Disclosed are certain partially fluorinated amide compounds and composite materials containing the compounds. Also disclosed are methods for making the composite materials.

13 Claims, 2 Drawing Sheets

PARTIALLY FLUORINATED UREAS AND AMIDES

This application is a DIV of Ser. No. 11/837,653, filed Aug. 13, 2007, now U.S. Pat. No. 8,044,239.

FIELD OF INVENTION

The present invention relates to fluorinated compounds containing short perfluorinated alkyl chains. The compounds are useful as organogelators and surface treatment materials to provide oil- and water-repellency properties to substrates.

BACKGROUND

Various compositions are known to be useful as treating agents to provide surface effects to substrates. Surface effects include repellency to moisture, soil, and stains, and other effects, which are particularly useful for fibrous substrates and other substrates such as hard surfaces. Many such treating agents are fluorinated polymers or copolymers.

Most commercially available fluorinated polymers useful as treating agents for imparting repellency to substrates contain predominately eight or more carbons in the perfluoroalkyl chain to provide the desired repellency properties. Honda et al, in Macromolecules, 2005, 38, 5699-5705 teach that for perfluoroalkyl chains of greater than 8 carbons, orientation of the $R_f$ groups is maintained in a semi-crystalline configuration while for such chains having less than 6 carbon atoms, reorientation occurs. This reorientation decreases surface properties such as contact angle.

Ordering imposed upon perfluorinated alkyl groups by hydrogen bonding networks has been used in gelation of carbon dioxide and the formation of foams, as disclosed by Beckman et. al, in WO 00/35998.

There is a need for compositions that improve the repellency of treating agents for fibrous and/or porous substrates and hard surface substrates while using short chain perfluoroalkyl groups; for instance $C_6$ or less.

SUMMARY OF INVENTION

One aspect of the invention is a compound of formula (I)

wherein
$R_o$ is a divalent organic group having 2 to 40 carbon atoms;
L is a linking group selected from —NHC(O)NH— or —C(O)NH— wherein the left side of the linking group is bonded to $R_o$;
p is an integer of 0 or 1;
q is an integer of 2 to 10;
r is an integer of 1 to 10; and
$R_f$ is a linear or branched $C_1$-$C_6$ perfluoroalkyl group.

Another aspect of the invention is a composite material comprising a porous support and a porous nanoweb, wherein said porous nanoweb comprises fibrous structures of between about 10 nm and about 1000 nm effective average fiber diameter as determined with electron microscopy; said fibrous structures comprising one or more compounds of formula (I).

Another aspect of the invention is a method for making a composite material comprising a porous support and a porous nanoweb comprising:
(a) providing a porous support;
(b) providing a gelling mixture comprising one or more solvents and one or more organogelator(s);
(c) applying the gelling mixture to the porous support;
(d) inducing said organogelator(s) to form a nanoweb gel; and
(e) removing the solvent(s) from the nanoweb gel to provide a dry porous nanoweb coating on said porous support;
wherein said organogelator(s) comprises one or more compounds of formula (I).

Another aspect of the invention is a solid substrate having disposed thereon a composition comprising a compound of formula (I).

DETAILED DESCRIPTION

Figure 1A:
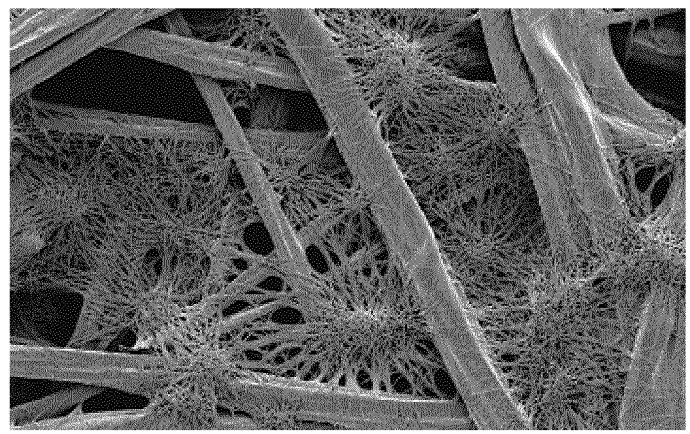
FIGS. 1A and B illustrate a scanning electron micrograph at 2000× and 10,000× magnification, respectively, of a composite according to an embodiment of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. Herein trademarks are designated by upper case. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

One aspect of the invention is a compound of formula (I)

wherein
$R_o$ is a divalent organic group having 2 to 40 carbon atoms;
L is a linking group selected from —NHC(O)NH— or —C(O)NH— wherein the left side of the linking group is bonded to $R_o$;
p is an integer of 0 or 1;
q is an integer of 2 to 10;
r is an integer of 1 to 10; and
$R_f$ is a linear or branched $C_1$-$C_6$ perfluoroalkyl group.

In various embodiments, in formula (I) $R_o$ is selected from: $C_2$-$C_{18}$ linear or branched alkyl group; $C_2$-$C_{18}$ linear or branched alkyl group substituted or interrupted by a $C_4$-$C_{16}$ cycloaliphatic group; $C_2$-$C_{18}$ linear or branched alkyl group substituted or interrupted by a $C_4$-$C_{16}$ aromatic group; $C_2$-$C_{18}$ linear or branched alkyl groups substituted or interrupted by a $C_4$-$C_{16}$ cycloaliphatic group and a $C_4$-$C_{16}$ aromatic group; $C_4$-$C_{16}$ cycloaliphatic group; $C_4$-$C_{16}$ aromatic group; and $C_4$-$C_{16}$ cycloaliphatic group having a $C_4$-$C_{16}$ aromatic group; wherein each aromatic group is optionally substituted with one or more Cl or Br; each alkyl and cycloaliphatic group is optionally substituted with one or two carbon-carbon double bonds; each group is optionally interrupted by one to two radicals selected from —O—, —S— and —$NR^3$—; and each group is optionally interrupted by one to four linkers selected from the group —S—, —N=, —OC(O)—, —C(O)$NR^3$—, —OC(O)$NR^3$—, —$NR^3$C(O)$NR^3$—; wherein $R^3$ is selected from: hydrogen and $C_1$-$C_4$ alkyl groups.

The term "wherein each aromatic group is optionally substituted with one or more Cl or Br" is meant to include aromatic groups substituted with one or more Cl or Br, as well as aromatic groups having no Cl or Br substituents. The term "each alkyl and cycloaliphatic group is optionally substituted with one or two carbon-carbon double bonds" is meant to include alkyl and cycloaliphatic groups having one or two carbon-carbon double bonds; as well as alkyl and cycloaliphatic groups that are fully saturated. In a preferred embodiment $R_o$ is selected from the group $C_2$-$C_{18}$ linear or branched alkyl group; and $C_2$-$C_{18}$ linear or branched alkyl group substituted, or interrupted by, a $C_4$-$C_{16}$ cycloaliphatic group; and most preferably $R_o$ is —$(CH_2)_6$—.

One preferred embodiment is a compound of formula (I) wherein L is —NHC(O)NH—, corresponding to a class of bis-ureas of formula (II):

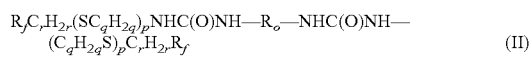

(II)

wherein p, q, r, $R_o$, and $R_f$ are as defined above. Compounds of formula (II) can be provided by condensation of diisocyanates with two equivalents of primary perfluoroalkyl alkyl amines. Typically a tertiary amine, for instance triethylamine, is used as catalyst, but other catalysts, or no catalyst, can be used if so desired. Typically a nonhydroxylic hydrocarbon solvent such as toluene or xylenes or a halocarbon such as dichloromethane (DCM) is used in the condensation.

Diisocyanates useful in the synthesis of bis-ureas of formula (II) include 2,4 and 2,6-toluene diisocyanate, 4,4'-diphenylmethane diisocyante (MDI), 1,3- and 1,4-phenylene diisocyanate, m- and/or p-xylylene diisocyanate (XDI), hexamethylene diisocyanate, tetramethylene diisocyanate, dodecamethylene diisocyanate, methyl pentamethylene diisocyanate, 2,2,4-trimethylhexamethylene diisocyanate, lysine diisocyanate, isophorone diisocyanate (IPDI), 1,3- and 1,4-diisocyanatocyclohexane, methyl cyclohexylene diisocyanate (hydrogenated TDI), dicyclohexylmethane-4,4'-diisocyanate (hydrogenated MDI). They are available from Bayer Inc., Pittsburgh, Pa., and Aldrich Chemical Co., Milwaukee Wis. Preferred are hexamethylene diisocyanate, methyl cyclohexylene diisocyanate, lysine diisocyanate, and isophorone diisocyanate. Most preferred is hexamethylene diisocyanate.

Another preferred embodiment is a compound of formula (III) wherein L is —C(O)NH—, corresponding to a class of bis-amides of formula (III):

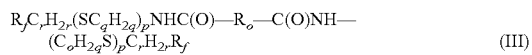

(III)

wherein p, q, r, $R_o$, and $R_f$ are as defined above. Compositions of formula (III) can be provided by condensation of diacid chlorides with two equivalents of primary perfluoroalkyl alkyl amines. The condensation is typically performed in the presence of a tertiary amine, for instance triethylamine, or other base. Typically a nonhydroxylic hydrocarbon solvent such as toluene or xylenes or a halocarbon such as dichloromethane (DCM) is used in the condensation.

Dicarboxylic acid chlorides useful in the synthesis of compositions of formula (III) include cyclohexane-1,4-dicarboxyl dichloride, succinoyl dichloride, adipoyl dichloride, suberoyl chloride, phthaloyl chloride, isophthaloyl chloride, and terephthaloyl chloride, all available from Aldrich Chemical Co or by synthesis. A preferred diacid chloride is suberoyl chloride.

The primary perfluoroalkyl alkyl amines useful in formation of compounds of formula (I) are available by synthesis using well-known synthetic methods. For instance, 1H,1H, 2H,2H-perfluoroalkyl amines are synthesized from corresponding iodides via treatment with sodium azide followed by reduction using Raney Ni as described in the literature procedure (Trabelsi, H.; Szoenyi, F.; Michelangeli, N.; Cambon, A. *J. Fluorine. Chem.*, 1994, 69, 115-117). The 2-(1H, 1H,2H,2H-perfluoroalkylthio)ethylamines can be prepared by the reaction of 1H,1H,2H,2H-perfluoroalkyl iodides with 2-aminoethanethiol as described in Rondestvedt, C. S., Jr.; et al, *J. Org. Chem.* 1977, 42, 2680. In a similar manner, reaction of 1H,1H,2H,2H-perfluoroalkyl iodides with 3-aminopropanethiol or 4-aminobutanethiol provides the corresponding 3-(1H,1H,2H,2H-perfluoroalkylthio)propylamines and 4-(1H,1H,2H,2H-perfluoroalkylthio)butylamines, respectively. Higher homologs of the w-aminoalkylthiols can be treated in a similar manner.

In all the embodiments of the invention disclosed herein, with regard to compounds of formula (I), preferably $R_f$ is a linear or branched $C_3$-$C_6$ perfluoroalkyl group.

The compounds of formula (I) are useful as organogelators, i.e. compounds that can self-assemble into fiber-like morphologies. Upon cooling a hot, homogeneous solution of a thermoreversible gelator in a gelling solvent for example, the gelator molecules associate via intermolecular hydrogen bonds to form fibers, which are bundles of H-bonded gelator molecules. If these fibrous bundles grow to be sufficiently long, they become entangled with one another like covalently-linked polymer chains to gel their solvent medium. The solvent can be removed from the gel to leave behind a network of assembled gelator fibers, a "nanoweb". Hence, organogelators can be used to obtain particular surface effects on porous or solid substrates and can be useful in the formation of nanoweb composites. Thus, another aspect of the invention is a composite material comprising a porous support and a porous nanoweb, wherein said porous nanoweb comprises fibrous structures of between about 10 nm and about 1000 nm effective average fiber diameter as determined with electron microscopy; said fibrous structures comprising one or more compounds of formula (I), as disclosed above. All the preferred embodiments disclosed above for the compounds of formula (I) are also applicable and included in the preferred embodiments of the composite material.

A further aspect of the invention is a method for making a composite material comprising a porous support and a porous nanoweb comprising:
 a) providing a porous support;
 b) providing a gelling mixture comprising one or more solvents and one or more organogelator(s);
 c) applying the gelling mixture to the porous support;
 d) inducing said organogelator(s) to form a nanoweb gel; and
 e) removing the solvent(s) from the nanoweb gel to provide a dry porous nanoweb coating on said porous support;
 wherein said organogelator(s) is one or more compounds of formula (I), as disclosed above. All the preferred embodiments disclosed above for the compounds of formula (I) are also applicable and included in the preferred embodiments of the method for making the composite material.

Suitable porous supports include woven and nonwoven fabrics, sheet materials and films, monolithic aggregates, powders, and porous articles such as frits and cartridges. Porous supports include: woven fabrics comprising glass, polyamides including but not limited to polyamide-6,6 (PA-66), polyamide-6 (PA-6), and polyamide-6,10 (PA-610), polyesters including but not limited to polyethylene terephthalate (PET), polytrimethylene terephthalate, and polybutylene terephthalate (PBT), rayon, cotton, wool, silk and combinations thereof; nonwoven materials having fibers of glass, paper, cellulose acetate and nitrate, polyamides, polyesters, polyolefins including bonded polyethylene (PE) and polypropylene (PP), and combinations thereof. Porous supports include nonwovens fabrics, for instance, polyolefins including PE and PP such as TYVEK® nonwoven fabric (flash spun PE fiber), SONTARA® nonwoven fabric (nonwoven polyester), and XAVAN® nonwoven fabric (nonwoven PP), SUPREL® nonwoven composite sheet, a nonwoven spunbond-meltblown-spunbond (SMS) composite sheet comprising multiple layers of sheath-core bicomponent melt spun fibers and side-by-side bicomponent meltblown fibers, such as described in U.S. Pat. No. 6,548,431, U.S. Pat. No. 6,797,655 and U.S. Pat. No. 6,831,025, herein incorporated by reference all trademarked products of E.I. du Pont de Nemours and Company; nonwoven composite sheet comprising sheath-core bicomponent melt spun fibers, such as described in U.S. Pat. No. 5,885,909, herein incorporated by reference; other multi-layer SMS nonwovens that are known in the art, such as PP spunbond-PP meltblown-PP spunbond laminates; nonwoven glass fiber media that are well known in the art and as described in Waggoner, U.S. Pat. No. 3,338,825, Bodendorf, U.S. Pat. No. 3,253,978, and references cited therein, hereby incorporated by reference; and KOLON® fabric, a spunbond polyester trademarked product of Korea Vilene. The nonwovens materials include those formed by web forming processing including dry laid (carded or air laid), wet laid, spunbonded and melt blown. The nonwoven web can be bonded with a resin, thermally bonded, solvent bonded, needle punched, spun-laced, or stitch-bonded. The bicomponent melt spun fibers, referred to above, can have a sheath of PE and a core of polyester. If a composite sheet comprising multiple layers is used, the bicomponent melt-blown fibers can have a PE component and a polyester component and be arranged side-by-side along the length thereof. Typically, the side-by-side and the sheath/core bicomponent fibers are separate layers in the multiple layer arrangement.

Preferred nonwoven porous supports include woven fabrics comprising glass, polyamides, polyesters, and combinations thereof; and nonwoven fabrics comprising glass, paper, cellulose acetate and nitrate, polyamides, polyesters, polyolefins, and combinations thereof. Most preferred porous supports include nonwoven bonded PE, PP, and polyester, and combinations thereof.

Other preferred nonwoven porous supports include electrospun nanofiber supports such as described by Schaefer, et al., in US 2004/0038014, hereby incorporated by reference; and electro-blown nanofiber supports disclosed in Kim, WO 2003/080905, hereby incorporated by reference. The nanofiber supports can be self-supporting or can be supported by other porous support layers. Preferably, the electropsun fiber supports are nanofiber supports comprised of nanofibers with an effective fiber diameter in the range of about 20 nm to about 1 μm, and preferably about 100 nm to about 750 nm. Suitable nanofiber supports include those derived from electro-spinning of polyester, polyamide, cellulose acetate, polyvinylidene fluoride (PVdF), polyacrylonitrile (PAN), polysulfone, polystyrene (PS), and polyvinyl alcohol (PVA). A preferred nanofiber porous support is incorporated into a layered structure comprising one or more other porous supports or scrims, for instance, nonwoven bonded PE or PP, and one or more layers of nanofiber, such as described in U.S. patent application Ser. No. 10/983,513 filed in November 2004, hereby incorporated by reference.

Other porous supports include microporous polymer films and sheet materials such as polyethersulfone, hydrophilic polyethersulfone, polyamide, PP, polytetrafluoroethylene (PTFE), and cellulose esters including cellulose acetate and nitrate. Microporous polymer films include stretched PTFE materials such as those manufactured by W.L. Gore and Associates, Inc. under the trade name GORE-TEX® membranes, and TETRATEX® PTFE membrane film, manufactured by the Donaldson Company; PP membranes; hydrophilic PP membranes, nitrocellulose membranes such as BIOTRACE™ NT membranes, modified nylon membranes such as BIO-INERT® membranes, PVdF membranes such as BIOTRACE™ PVDF membranes, polyethersulfone membranes such as OMEGA™ membranes, SUPOR® hydrophilic polyethersulfone membrane, ion exchange membranes such as MUSTANG™ ion exchange membranes, all brand names of Pall Life Sciences; nylon membranes disclosed in U.S. Pat. No. 6,413,070 and references cited therein, herein incorporated by reference. Preferred microporous polymer films are polyethersulfone, hydrophilic polyethersulfone, polyamide, PP, PTFE, and cellulose esters.

Porous supports can also be solid substrates. Solid substrates useful as porous supports for the invention are stone, masonry, concrete, unglazed tile, brick, porous clay, granite, limestone, grout, mortar, marble, wood, gypsum board, terrazzo, or composite materials.

An organogelator is defined herein as a non-polymeric organic compound whose molecules can establish, between themselves, at least one physical interaction leading to a self-assembly of the molecules in a carrier fluid, with formation of a 3-D network, also called a "nanoweb gel", that is responsible for gelation of the carrier fluid. The nanoweb gel may result from the formation of a network of fibrous structures due to the stacking or aggregation of organogelator molecules. Depending on the nature of the organogelator, the fibrous structures have variable dimensions that may range up to one micron, or even several microns. These fibrous structures include fibers, strands and/or tapes.

The term "gelling" or "gelation" means a thickening of the medium that may result in a gelatinous consistency and even in a solid, rigid consistency that does not flow under its own weight. The ability to form this network of fibrous structures, and thus the gelation, depends on the chemical structure of the organogelator, the nature of the substituents, the nature of the carrier fluid, and the particular temperature, pressure, concentration, pH, shear conditions and other parameters that may be used to induce gelation of the medium. The nanoweb gels can be reversible. For instance, gels formed in a cooling cycle may be dissipated in a heating cycle. This cycle of gel formation can be repeated a number of times since the gel is formed by physical, non-covalent interactions between gelator molecules, such as hydrogen bonding.

The composites can be made using a nanoweb gel that comprises a nanoweb phase and a fluid phase, which, upon removal of the fluid, forms a porous interpenetrating nanoweb. It has been found that this capability is strongly dependent upon the particular structural characteristics of the organogelator and particular processing parameters including the nature of the solvent, temperature, gelator concentration, method of solvent removal, and the nature of the porous support.

Solvents and specific conditions for forming gels of many organogelators are available in the patent and scientific literature. However, the one skilled in the art will recognize that many specific gelators may require some preliminary gelling experimentation. For such cases, a methodology has been developed for matching a solvent system with specific gelators to allow efficient gel formation. In general, if the gelator is too soluble, it will dissolve without forming a gel even at high concentrations. If the gelator is not soluble enough, it may or may not dissolve at high temperature, but precipitate again as the temperature is lowered. Ideally, the organogelator should dissolve in a solvent at some temperature and assemble into a network upon cooling. Preferably the gelators have a solubility in a solvent system of about 0.1 to 5 wt % at a temperature/pressure above the gel point. Changing the temperature and/or pressure, adjusting the solvent composition, adjusting the pH, altering the shear-state of thixotropic systems, or a combination of parameters can be used to induce gelling.

A simple screening protocol for evaluating thermo-reversible gels allows evaluation of a specific gelator with different solvents in parallel using a reactor block. In a typical set-up, 1-2 wt % slurries of the organogelator in solvents of varying polarities can be prepared, for example a series may include: water, n-butanol, ethanol, chloroform, toluene, and cyclohexane. The vials are then placed in a reactor block for 1 h while stirring at a temperature close to the boiling point of the solvent to induce dissolution. In the case of some gelators, for instance, urea-based gelators, additives such as lithium salts, for instance lithium nitrate, can be added in small amounts (0.1 to about 10 wt %, based on the amount of organogelator) as described in U.S. Pat. No. 6,420,466, hereby incorporated by reference. Upon cooling, gelation may occur and is evident by formation of a translucent to opaque appearance without the formation of solid crystals, and/or a significant increase in viscosity. If gelation does not occur, one can screen different solvents or solvent mixtures as well as different additives and additive levels. If a gelator sample is soluble in a given solvent, but gelation does not occur, then one can either raise the gelator concentration to, for instance, 3 or 5 wt % and repeat the heating cycle, or one can lower the solubility of the compound by using a solvent mixture of lower polarity.

Preferred solvents for H-bonded organogelators are those having H-bonding capability that allows disruption of intermolecular H-bonding between solute molecules. Water, ammonia, alcohols, sulfoxides, esters, ethers, amines, amides, and lactams are useful. H-bonded organogelators often exhibit very high solubility in the lower alcohols such as methanol and ethanol. Whereas H-bonded organogelators often exhibit lesser solubility in the higher aliphatic and cyclic alcohols including propanol, butanol, hexanol, cyclohexanol and isomers thereof, making them more desirable for use as gelating solvents. Specific solvents that are especially useful in forming gelling mixtures include: water, the lower aliphatic and cyclic alcohols such as ethanol, isopropyl alcohol, butanol, hexanol, cyclohexanol, cyclopentanol, and octanol; aliphatic and aromatic hydrocarbons such as hexane, cyclohexane, heptane, octane, toluene, xylenes, and mesitylene; amides and lactams such as N-methylpyrrolidone, pyrrolidone, caprolactam, N-methyl caprolactam, dimethyl formamide, and dimethyl acetamide; ethers such as dibutyl ether, dipropyl ether, methyl butyl ether; ether alcohols such as 2-methoxyethanol, 2-butoxyethanol, and others in the class of ethers known as CELLUSOLVES®; esters such as ethyl acetate, butyl acetate and the like; aliphatic and aromatic halocarbons such as dichloromethane, 1,2-dichloroethane, 1,1,1-trichloroethane and dichlorobenzene.

A preferred solvent for the fluorinated H-bonded organogelators disclosed herein is supercritical carbon dioxide ($scCO_2$). An advantage of $scCO_2$ is that the solvent is environmentally friendly relative to typical organic solvents; and can be readily removed after gel formation by slow venting of the carbon dioxide. In addition, $scCO_2$ is an attractive medium for preparing composites from organogelators because the solvent and transport properties of the supercritical fluid solution (e.g., the solution density) can be varied appreciably and continuously with relatively minor changes in temperature or pressure. Thus, the solvent environment can be optimized for a specific gelation application by tuning the various density-dependent fluid properties.

A fluid is in the supercritical fluid state when the system temperature and pressure exceed the corresponding critical point values defined by the critical temperature ($T_C$) and pressure ($P_C$). For pure substances, the critical temperature and pressure are the highest at which vapor and liquid phases can coexist. Above the critical temperature, a liquid does not form for a pure substance, regardless of the applied pressure. Similarly, the critical pressure and critical molar volume are defined at this critical temperature corresponding to the state at which the vapor and liquid phases merge. Similarly, although more complex for multicomponent mixtures, the mixture critical state is identified as the condition at which the properties of coexisting vapor and liquid phases become indistinguishable. For a discussion of supercritical fluids, see Kirk-Othmer Encycl. of Chem. Technology, $4^{th}$ Ed., Vol. 23, pg. 452-477.

The gelling mixture, as applied to a solid or porous support, can be in the form of a homogeneous isotropic solution; a gel that can be shear-thinned (thixotropic) to form a fluidized gel; or a gel in the form of a film, sheet or powder that can be melted to form a fluidized gel. Formulation of a suitable gelling mixture depends upon the methods anticipated for applying the gelling mixture and gelling the impregnated or coated support. For instance, in a preferred embodiment the gelling mixture is a gel that can be shear-thinned prior to, or during, application to form a fluidized gel. The fluidized gel can then penetrate a porous support to provide an impregnated support.

In another preferred embodiment the gelling mixture is a homogeneous isotropic solution that, if so desired, is heated above ambient conditions. After applying the solution to provide a coated or impregnated support, the treated support can be cooled to induce gelation. Suitable gelling mixtures preferably comprise 0.01 to 20 wt % of one or more organogelators, and preferably, 0.5 to 5 wt %, with the remainder being solvent and other processing aids, for instance lithium salts.

Applying the gelling mixture to a solid or porous support can be done by a variety of methods including one or more of the steps of: spraying, coating, blading, casting laminating, rolling, printing, dipping, and immersing; and allowing gravity, diffusion, and/or flow through of the gelling mixture into the porous support, and, optionally, applying pressure, heat or vacuum. Spraying, coating, blading, casting and immersing are preferred methods for applying thixotropic gels and spraying and blading are most preferred. Laminating and heating is a preferred method for applying solid gels in the form of films. Spraying, coating, blading, casting, printing and immersing or dipping are preferred methods for applying homogeneous isotropic solutions. In some instances, it is advantageous to remove excess gelling mixture from the surface of a porous support, such as by scraping or the like.

Gelling the treated support can be accomplished by a variety of methods depending upon the nature of the gelling mixture. In one preferred embodiment, wherein the gelling mixture is a thermo-reversible gel, the gelling step comprises cooling of a homogeneous solution of the gelling mixture in the impregnated support. The gelling mixture can be preheated to provide a homogeneous solution or can be cooled from ambient temperature, if so desired. Another preferred embodiment, wherein the gelling mixture is a gel applied with shearing, the gelling step can comprise abating the shearing in the impregnated support. This can be accomplished by allowing the impregnated support to sit for a period of time in the absence of shear. In another embodiment, wherein the gelling mixture is sensitive to pH, the impregnated support can be subjected to a change in pH. In other embodiments the solvent can be modified by addition of a non-solvent in a solvent exchange or partially removed to provide a gel.

Drying the gel, or removing the solvent from the gel, will leave behind a porous nanoweb on and/or within a solid or porous support. Drying can be achieved through a variety of routes including freeze drying, ambient drying, oven, radiant and microwave heating, vacuum drying (with or without heat), or critical point drying (CPD). Alternatively the solvent can be exchanged with another fluid, in a fluid-fluid extraction process or a supercritical fluid extraction (SFE) process, which then can be removed from the gel via one of the aforementioned drying techniques, if so desired. When $scCO_2$ is used as the solvent, it may be removed from the gel by slowly venting the $CO_2$.

The drying method can have a profound effect on the resultant nanoweb structure as the various drying methods occur over different time scales, place different stresses on the nanoweb structure, and involve the crossing of different phase boundaries.

In vacuum drying, the driving force for solvent removal from the impregnated material is increased such that the solvent can be removed more readily, and thus without disruption of the assembled nanoweb. Heat can be used in combination with vacuum if it does not disrupt the gelled assembly. Ambient drying is performed at atmospheric pressure and optionally with heat. In freeze drying, the coated or impregnated material is rapidly frozen (on a time scale that does not allow for rearrangement of the gel structure) and solvent is subsequently sublimed away to provide the nanoweb material.

The compounds of formula (I) can also be used as surface treatment agents for solid substrates, for instance stone and tile, as defined above. Thus, another aspect of the invention is a solid substrate having disposed thereon a composition comprising a compound of formula (I), as disclosed above. All the preferred embodiments disclosed above for the compounds of formula (I) are also applicable and included in the preferred embodiments of the solid substrate having disposed thereon a composition comprising formula (I). The composition comprising compounds of formula (I) can be applied to solid substrates using the method for making a composite material disclosed above, wherein the porous support is a solid substrate; or, if so desired, the solid substrate can be treated with a homogeneous solution comprising the compound of formula (I) and allowed to dry.

For fibrous substrates, the amount of composition of formula (I) applied, in order to obtain a nanoweb composite material, is about 0.1 to about 2.0 wt %, and preferably 0.1 to about 1 wt %, based on the dry wt of substrate. For fibrous substrates, the treated substrate preferably has about 100 micrograms per gram to about 10,000 micrograms per gram fluorine, and more preferably about 100 micrograms per gram to about 1000 micrograms per gram fluorine, based on the weight of the dried substrate; to provide significant surface treatment properties such as increases in water and oil contact angles.

For solid substrates such as stone and tile, the treated substrate preferably contains about 100 micrograms per gram to about 1000 micrograms per gram fluorine based on the weight of the dried substrate; to provide significant surface treatment properties such as increases in water and oil contact angles.

Figure 1B:
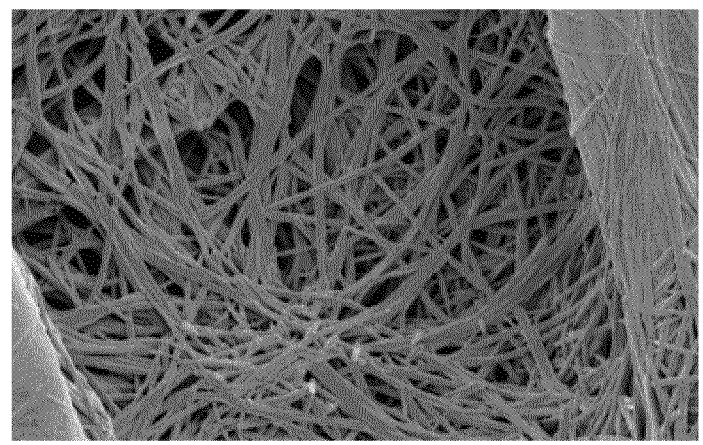
Figure 2:
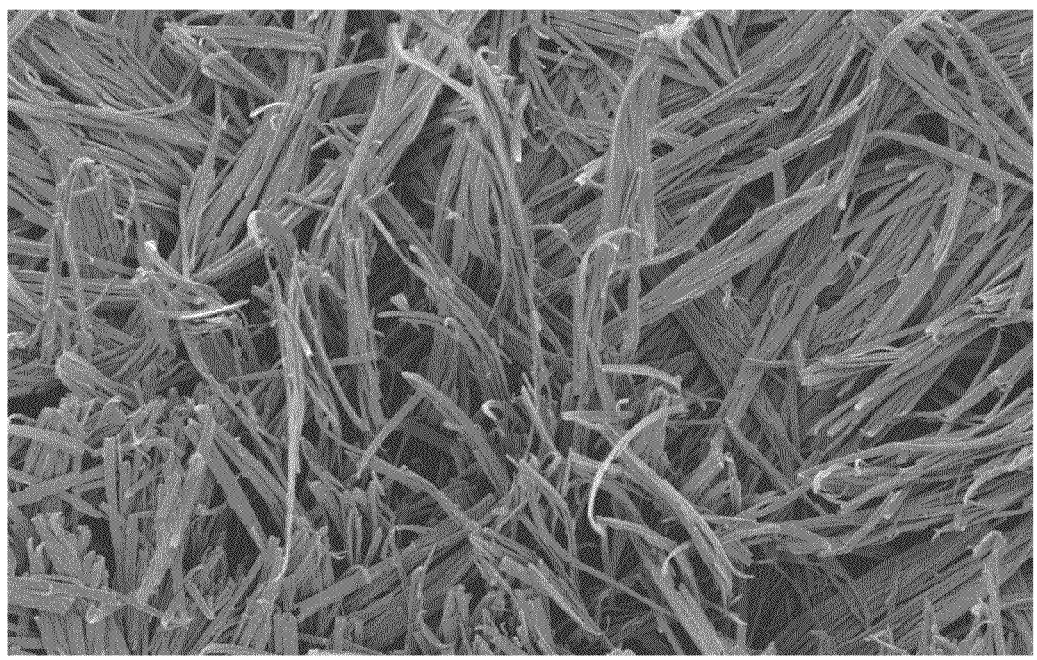
FIG. 2 illustrates a scanning electron micrograph at 2000× magnification of a composite according to one embodiment of the invention.

The nanoweb composites can be characterized by scanning electron microscopy. FIGS. 1A and B, and FIG. 2 show various composite structures of the invention. In FIG. 1A the larger fibers are the nonwoven porous support and the fine structures are the nanoweb. FIG. 1B shows the detailed structure of a separate nanoweb.

The porous nanoweb composites and treated solid substrates can be characterized by a quantitative estimation of the surface tension relative to that of the support. Surface tension is typically characterized by measuring the contact angle of a water droplet or other liquid substance, contacting the surface in the advancing and receding dynamic modes. An advancing contact angle is measured as a liquid droplet is increasing in size and advancing on the surface of a substrate. A receding contact angle is measured as a liquid droplet is decreasing in size and receding on the surface of a substrate. Contact angles can also be measured in a static mode. This is a well known method for determining surface properties and is discussed in detail in Physical Chemistry of Surfaces, 4th Ed., Arthur W. Adamson, John Wiley & Sons, 1982, pp. 338-361. The water contact angle is a quantitative measurement of the hydrophobicity of a surface. The higher the hydrophobicity, the higher will be the contact angle of the water droplet. Surfaces exhibiting water droplet advancing contact angles of greater than 150° are considered super-hydrophobic. The details of contact angle measurements are discussed in the examples. Preferred nanoweb composites of the invention are characterized by water droplet advancing contact angle of greater than 130°. Other preferred composites of the invention are characterized by a static hexadecane droplet contact angle of about 70° or greater, indicating oleophobicity.

The composite materials can be used as gas-solid filter. The gas can be air, carbon dioxide, oxygen, nitrogen, a noble gas, or any other process gas used in industrial or commercial processes. Air filters are preferred applications of the composite materials. Filters can be in the form of nonwoven pleated or unpleated cartridge filters, glass or other ceramic microfiber filters.

Since the individual organogelator molecules making up the nanoweb are not covalently bonded to one another, there are conditions in which the porous nanoweb can be easily dissolved and removed from the porous support. In applications wherein trapped material is of significant interest, for instance, biological material, radioactive material, etc., the solubility of the nanoweb is a particular advantage, as it can allow release and recovery of the trapped material. Such flexibility can be useful in recycling and recovery of composite materials as well.

The composite materials of various embodiments may also find use in barrier fabric applications, such as for protective clothing or construction wrap, in which good barrier against liquid penetration is provided while maintaining good air and moisture vapor permeability.

EXAMPLES

These examples are illustrative and are not to be read as limiting the scope of the invention as it is defined by the appended claims.

Materials and Methods

The following abbreviations are used in the examples:
DMF=dimethylformamide
DMSO=Dimethyl sulfoxide
mp=melting point
MPa=mega-Pascal ($10^6$ Pascals, 1 bar=0.100 MPa)
RT=room temperature
TEA=triethyl amine
TFA=trifluoroacetic acid THF=tetrahydrofuran All solvents and reagents, unless otherwise indicated, were purchased from Commercial Sources and used directly as supplied. 1H,1H,2H,2H-perfluorohexylamine was synthesized from corresponding iodides via the azide followed by reduction using Raney Ni as described in the literature procedure (Trabelsi, H.; Szoenyi, F.; Michelangeli, N.; Cambon, A. *J. Fluorine. Chem*, (1994), 69, 115-117). 2-(1H,1H,2H,2H-perfluorohexylthio)ethylamine was prepared by the reaction of 1H,1H,2H,2H-perfluoroalkyl iodides with 2-aminoethanethiol as disclosed in the literature procedure (Rondestvedt, C. S., Jr.; Thayer, G. L., Jr. *J. Org. Chem.* (1977), 42, 2680). $^1$H and $^{19}$F NMR spectra were recorded on a Brucker DRX 400 or 500 Spectrometer. Chemical shifts have been reported in ppm relative to an internal reference ($CDCl_3$, $CFCl_3$ or TMS). All melting points reported were uncorrected.

Method 1. Gel-Impregnation on Nonwoven Supports

Nonwoven fabrics: TYVEK® polyethylene nonwoven fabric (E.I. du Pont de Nemours, Wilmington Del.); and KOLON® 70 gsm spunbound polyester fabric (Korea Vilene Inc)] (about 3.0-3.0 cm squared) were immersed in a suspension of a gelator in organic solvent kept in closed reaction flask equipped with a stir bar and temperature controller. The mixtures were heated 5° C. below the boiling point of the solvent for 1-2 h until clear solutions formed. The flasks were then either rapidly cooled to RT by removing the oil bath or slowly cooled to RT by switching off the heat. Gel formation was usually observed in 0.5 h to about 6 h time and the gels were allowed to age for additional 6 h. The gelator impregnated samples removed and dried in a vacuum oven at RT overnight. The dried samples were weighed and used for contact angle measurements.

Method 2. Gel-Impregnation on Nonwoven Supports in $CO_2$

Samples of TYVEK® and KOLON® 70 gsm nonwoven fabrics identical to those of Method 1 were mounted in a high-pressure variable volume view cell which had been charged with gelator and equipped with a TEFLON-coated stir bar and an electrical heating jacket. The cell was sealed and then charged with liquid $CO_2$ to give a final gelator concentration of 0.2-0.5 wt %. The cell was then heated to about 70° C. and pressurized to about 210 bar (21.0 MPa) with agitation to solubilize a significant portion of the gelator. Agitation was then suspended and the cell was slowly cooled to room temperature over several hours at constant pressure to allow gel formation within and upon the nonwoven fabric samples. The $CO_2$ was then slowly vented from the view cell, and the gelator impregnated samples were removed, imaged by scanning electron microscopy, and utilized for contact angle measurements.

Example 1

Compound 1

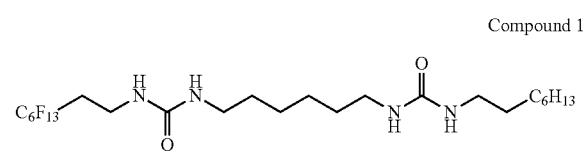

This example illustrates the synthesis of Compound 1 of the invention.

To a mixture of 1H,1H,2H,2H-perfluorooctylamine (1.81 g, 5.0 mmol) and TEA (0.02 g, 0.2 mmol) in dry DCM (15 mL), under nitrogen atmosphere and cooled to 0° C., was added drop-wise 1,6-diisocyanatohexane (0.420 g, 2.5 mmol). The mixture was slowly warmed to RT, and stirred for 3 h. The precipitated urea was filtered and washed repeatedly with cold DCM. The resulting solid was dried to provide Compound 1 (2.0 g): mp 156.8-158.5° C.; $^1$H NMR (methanol-d4): δ 3.41 (t, J=6.8 Hz, 4H) 3.06 (t, J=6.8 Hz, 4H), 2.34 (m, 4H), 1.46 (m, 4H), 1.34 (m, 4H); $^{19}$F NMR (methanol-d4): δ −81.4 (m, 6F), −114.2 (m, 4F), −121.8 (s, 4F), −122.8 (s, 4F), −123.7 (s, 4F), −126.3 (m, 4F).

Example 2

Compound 2

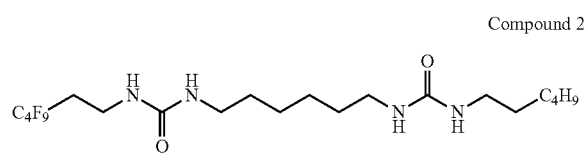

Using a similar procedure as described in Example 1, reaction of 1H,1H,2H,2H-perfluorohexylamine (2.10 g) with of 1,6-diisocyanatohexane (0.672 g) provided Compound 2 (2.18 g): mp 130-131.8° C.; $^1$H NMR (methanol-d4): δ 3.45 (t, J=6.8 Hz, 4H) 3.10 (t, J=6.8 Hz, 4H), 2.35 (m, 4H), 1.48 (m, 4H), 1.35 (m, 4H); $^{19}$F NMR (methanol-d4): δ −81.7 (m, 6F), −114.4 (m, 4F), −124.7 (m, 4F), −126.2 (m, 4F).

Example 3

Compound 3

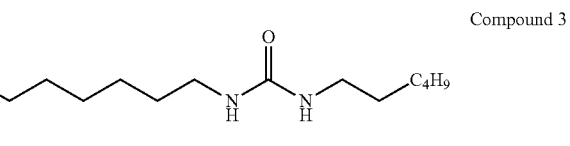

This example illustrates the synthesis of Compound 3 of the invention. To a solution of 1,8-diisocyanatooctane (1.4 g, 6.9 mmol) in dry chloroform (25 mL), cooled to −5° C., was added and 1H,1H,2H,2H-perfluorohexylamine (3.6 g, 13.8 mmol) dropwise under nitrogen atmosphere, maintaining temperature below 0° C. The reaction was slowly warmed to RT and stirred overnight. The resulting precipitate was isolated by filtration, rinsed with diethyl ether and dried to provide Compound 3 (5.0 g). $^1$H NMR (TFA-d): δ 3.81 (4H), 3.30 (br, 4H), 2.52 (br, 4H), 1.70 (br, 4H), 1.40 (br, 8H); $^{19}$F NMR (TFA-d): δ −89.4 (6F), −122.1 (4F), −132.3 (4F), −133.7 (4F).

Example 4

Compound 4

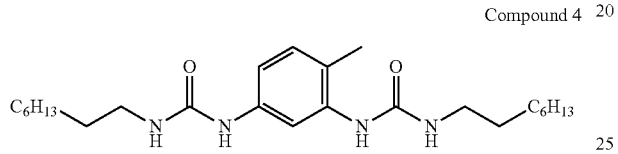

This example illustrates the synthesis of Compound 4 of the invention. To a solution of 2,4-tolylene diisocyanate (0.435 g) in dry DCM (15 mL), was added and 1H,1H,2H,2H-perfluorohexylamine (2.0 g) dropwise under nitrogen atmosphere at rt. The mixture stirred for 10 h at RT and the solid formed was filtered, washed with cold DCM and dried to obtain Compound 4 as a off-white solid (2.1 g): $^1$H NMR (Acetone d6) δ 7.79 (s, 2H), 7.67 (dd, J=6.4, 2.0 Hz, 1H), 7.13 (d, J=2.0 Hz, 1H), 6.83 (d, J=8.0 Hz, 1H), 6.1 (bs, 2H), 3.44 (q, J=6.8 Hz, 4H), 2.39 (m, 4H), 1.99 (s, 3H); $^{19}$F NMR (Acetone d6) δ −82.1 (tt, J=10, 2 Hz, 6F), −114.8 (m, 4F), −122.6 (m, 4F), −123.8 (m, 4F), −124.6 (m, 4F), −127.1 (m, 4F).

Example 5

Compound 5

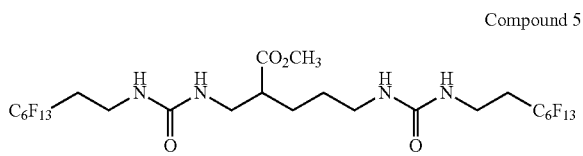

Using a similar procedure as described in Example 3, reaction of lysine diisocyanate (1.1 g) with 1H,1H,2H,2H-perfluorooctylamine (3.9 g) provided compound 5 (5.05 g): $^1$H NMR (TFA-d): δ 4.58 (m, 1H), 3.90 (s, 3H), 3.76, 3.70, 3.33 (t, 2H each, J=6.4 Hz), 2.55-2.37 (m, 4H), 1.83, 1.74 (m, 1H each), 1.71, 1.54 (m, 2H each); $^{19}$F NMR (TFA-d): δ −89.9 (6F), −112.5 (4F)-129.6 (4F), −131.0 (4F), −132.0 (4F), −134.6 (4F); $^{13}$C NMR (TFA-d): δ 178.1, 162.3, 161.8, 56.5, 55.6 43.7, 36.4, 35.8, 33.7, 32.9 (t), 32.6 (t), 29.7, 24.6.

Example 6

Compound 6

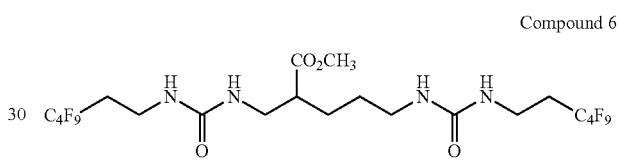

Using a similar procedure as described in Example 3, reaction of lysine diisocyanate (1.4 g) with 1H,1H,2H,2H-perfluorohexylamine (3.6 g) provided Compound 6 (5.05 g): $^1$H NMR (TFA-d): δ 4.57 (br, 1H), 3.91 (s, 3H), 3.77, 3.71, 3.34 (m, 2H), 2.46 (br, 4H), 2.00, 1.83 (br, 1H each), 1.72, 1.53 (br, 2H each); $^{19}$F NMR (TFA-d): δ −89.4 (6F), −122.0 (4F), −132.2 (4F), −133.6 (4F); $^{13}$C NMR (TFA-d): 178.1, 162.4, 161.8, 56.5, 55.7, 43.7, 36.4, 35.8, 33.7, 32.8, 32.6, 29.8, 24.6.

Example 7

Compound 7

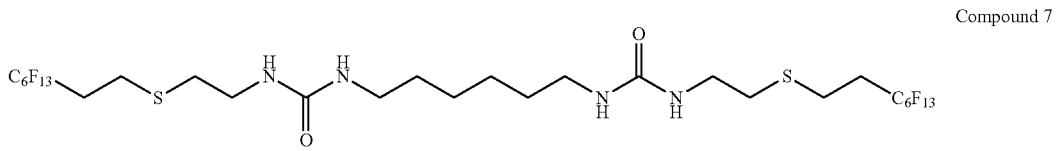

Using a similar procedure as described in Example 1, reaction of 2-(1H,1H,2H,2H-perfluorooctylthio)ethylamine (4.23 g) with of 1,6-diisocyanatohexane (0.84 g) provided Compound 7 (4.3 g): mp 176.8-177.5° C.; $^1$H NMR (DMF-d7 100° C.): δ 5.84 (bs, 2H), 5.73 (bs, 2H), 3.38 (q, J=6.4 Hz, 4H), 3.15 (q, J=6.8 Hz, 4H), 2.83 (t, J=6.4 Hz, 4H), 2.73 (t, J=6.8 Hz, 4H), 2.57 (m, 4H), 1.56 (m, 4H), 1.35 (m, 4H); $^{19}$F NMR (DMF-d7 100° C.): δ −81.4 (m, 6F), −113.4 (m, 4F), −121.7 (m, 4F), −122.7 (m, 4F), −123.2 (s, 4F), −126.0 (m, 4F)

Example 8

To a mixture of 1H,1H,2H,2H-perfluorooctylamine (3.6 g, 9.9 mmol), DCM (30 mL) and TEA (0.999 g, 9.9 mmol) under a N$_2$ purge was added suberoyl chloride (0.949 g, 4.5 mmol) and the mixture stirred for 12 h at RT. The reaction mixture was concentrated to half its volume and filtered. The solid product was washed with cold DCM (5 mL) followed by 1% HCl (2×5 mL), water (2×5 mL) and finally with hexanes (2×5 mL). The resulting solid was recrystallized from methanol to provide Compound 9: mp 114.1-115.2° C.; $^1$H NMR (methanol-d4): δ 3.48 (t, J=6.8 Hz, 4H), 2.39 (m, 4H), 2.18 (t, J=7.6 Hz, 4H), 1.59 (m, 4H), 1.34 (m, 4H); $^{19}$F NMR (metha- Compound 8

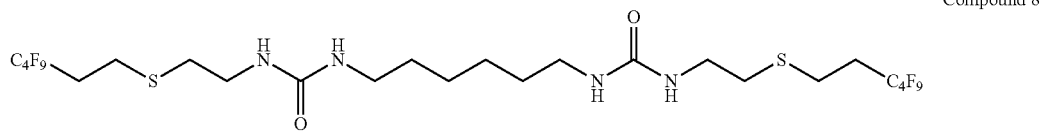

Using a similar procedure as described in Example 1, reaction of 2-(1H,1H,2H,2H-perfluorohexylthio)ethylamine (1.94 g) with of 1,6-diisocyanatohexane (0.504 g) provided Compound 8 (1.97 g): mp 160-162° C.; $^1$H NMR (DMF-d7 100° C.): δ 5.85 (bs, 2H), 5.74 (bs, 2H), 3.39 (q, J=6.4 Hz, 4H), 3.13 (q, J=6.8 Hz, 4H), 2.84 (t, J=6.4 Hz, 4H), 2.72 (t, J=6.8 Hz, 4H), 2.58 (m, 4H), 1.55 (m, 4H), 1.35 (m, 4H); $^{19}$F NMR (DMF-d7 100° C.): δ −81.6 (m, 6F), −113.5 (m, 4F), −124.2 (m, 4F), −125.8 (m, 4F).

nol-d4): δ −84.3 (m, 6F), −117.1 (m, 4F), −124.6 (m, 4F), −125.9 (m, 4F), −126.6 (m, 4F), −128.9 (m, 4F).

Example 10

Compound 10

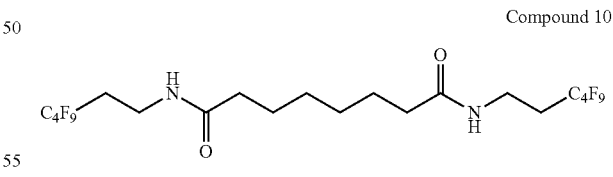

Example 9

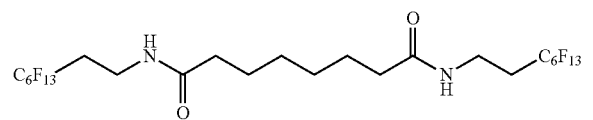

This example illustrates the synthesis of compound 9 of the invention.

Using a similar procedure as described in Example 9, reaction of 1H,1H,2H,2H-perfluorohexylamine (2.6 g) with suberoyl chloride (0.949 g) provided Compound 10 (3.2 g): mp 114.1-115.2° C.; $^1$H NMR (methanol-d4): δ 3.51 (t, J=6.8 Hz, 4H), 2.41 (m, 4H), 2.20 (t, J=7.6 Hz, 4H), 1.63 (m, 4H), 1.36 (m, 4H); $^{19}$F NMR (methanol-d4): δ −83.1 (m, 6F), −116.0 (m, 4F), −126.1 (m, 4F), −127.6 (m, 4F).

Example 11

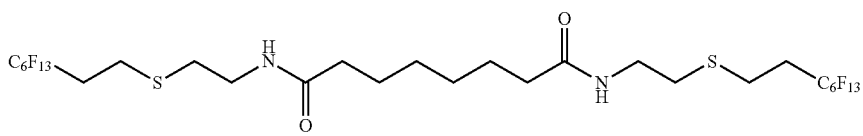

Compound 11

By using a similar procedure as described in Example 9, reaction of 2-(1H,1H,2H,2H-perfluorooctylthio)ethylamine (2.09 g) with suberoyl chloride (0.475 g) provided Compound 11 (3.2 g): mp 144.8-146.2° C.: $^1$H NMR (acetone-d6): δ 7.22 (bs, 2H), 3.42 (q, J=6.0 Hz, 4H), 2.86 (t, J=6.4 Hz, 4H), 2.75 (t, J=6.8 Hz, 4H), 2.57 (m, 4H), 2.16 (t, J=7.2 Hz, 4H), 1.59 (m, 4H), 1.35 (m, 4H); $^{19}$F NMR (acetone-d6): δ −82.1 (m, 6F), −115.0 (m, 4F), −122.8 (m, 4F), −123.8 (m, 4F), −124.2 (s, 4F), −126.2 (m, 4F).

Example 12

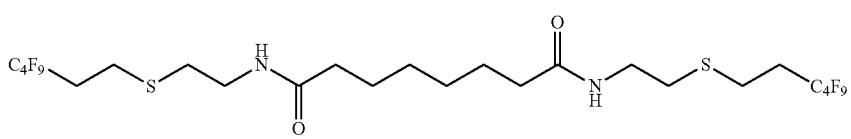

Compound 12

By using a similar procedure as described in Example 9, reaction of 2-(1H,1H,2H,2H-perfluorohexylthio)ethylamine (1.59 g) with suberoyl chloride (0.475 g) provided Compound 12 (1.4 g): mp 122-123.5° C.; $^1$H NMR (acetone-d6): δ 7.22 (bs, 2H), 3.40 (q, J=6.0 Hz, 4H), 2.85 (t, J=6.4 Hz, 4H), 2.75 (t, J=6.8 Hz, 4H), 2.55 (m, 4H), 2.15 (t, J=7.2 Hz, 4H), 1.56 (m, 4H), 1.37 (m, 4H); $^{19}$F NMR (acetone-d6): δ −82.4 (m, 6F), −116.2 (m, 4F), −126.2 (m, 4F), −127.7 (m, 4F).

Example 13

This example illustrates gelation in organic solvents.

Generally 0.5-3 wt % of a gelator in an organic solvent in a closed vial was heated to 5-10° C. below the boiling point of the solvent in a reactor block until a clear solution was obtained. The vials were allowed to cool at RT either by a slow cool by switching of the heat or by transferring the vials to a constant temperature water bath kept at RT. The state of the solution was evaluated after 2-12 h. Stable gel formation was tested by inversing the vial. Compounds 1, 7 and 8 gelled a variety of the organic solvents ranging various polarities, whereas Compounds 2-6 and 9-12 gelled more selectively. The results are summarized in Table 1 and 2.

TABLE 1

Gel Characteristics for Compounds

| | Gelator (wt %) | | |
|---|---|---|---|
| Solvent | Compound 1 | Compound 7 | Compound 8 |
| Toluene | Hazy (1) | Hazy (2) | Hazy (2) |
| Xylene | Hazy (1) | Hazy (1.5) | Hazy (2) |
| Chloroform | Hazy (3) | Precipitate (2) | Partial (2) |

TABLE 1-continued

Gel Characteristics for Compounds

| | Gelator (wt %) | | |
|---|---|---|---|
| Solvent | Compound 1 | Compound 7 | Compound 8 |
| THF | Transparent (1) | Hazy (2) | Opaque (2.5) |
| Acetone | Transparent (1) | Opaque (2) | Opaque (3) |
| Acetonitrile | Hazy (1) | Opaque (2) | Opaque (2) |
| Ethyl acetate | Transparent (1) | Partial (2) | Hazy (3) |
| DMF | Transparent (1) | Transparent (1) | Transparent (2) |

TABLE 1-continued

Gel Characteristics for Compounds

| | Gelator (wt %) | | |
|---|---|---|---|
| Solvent | Compound 1 | Compound 7 | Compound 8 |
| DMSO | Opaque (1) | Transparent (1) | Transparent (2) |
| Dimethyl acetamide | Transparent (2) | Transparent (1) | Partial (2) |
| N-methylpyrolidone | Hazy (1) | Partial (1.5) | Clear Solution (2) |
| Pyridine | Hazy (1) | Partial (1.5) | Hazy (2) |
| n-Butanol | Transparent (1) | Transparent (1.5) | Hazy (2) |
| Isopropanol | Transparent (1) | Transparent (1.5) | Hazy (2) |
| Methanol | Hazy (1) | Opaque (1.5) | Transparent (4) |
| Ethanol | Transparent (2) | Hazy (1.5) | Hazy (3) |

[†]Number in parenthesis indicates minimum gel concentration. Hazy: solid gel partially transparent; transparent: solid gel completely transparent; opaque: solid gel, not transparent; partial: solid or semi-moving gel that has some free flowing liquid in it; precipitate: more like a precipitate than a gel.

TABLE 2

Gel Characteristics for Compounds

| | Gelation conditions | | |
|---|---|---|---|
| Compound | Wt % gelator | Solvent | Appearance[†] |
| Compound 2 | 2-3 | Methanol, n-butanol | Partial/Precipitate |
| | 1-2 | Toluene, THF, Acetone, DMF, DMSO | Clear solution |
| Compound 3 | 2 | DMSO | Partial |

TABLE 2-continued

Gel Characteristics for Compounds

| Compound | Wt % gelator | Solvent | Appearance[†] |
|---|---|---|---|
| Compound 4 | 2.5 | Acetonitrile | Partial |
|  | 1-2 | Ethanol, acetone, DMF, DMSO, THF, ethyl acetate | Clear solution |
| Compound 5 | 2 | Acetonitrile | Transparent |
|  | 2 | Toluene | Hazy |
| Compound 6 | 2 | DMSO | Partial |
|  | 2 | Toluene, Ethanol, acetone, acetonitrile, THF, ethyl acetate | Cloudy solution |
| Compound 9 | 1-2 | DMF | Transparent |
|  | 2 | DMSO | Opaque |
| Compound 10 | 2 | DCM | Opaque |
| Compound 11 | 1 | DMSO | Opaque |
|  | 2 | DMF | Hazy |
| Compound 12 | 3 | DCM | Partial |

[†]Same meaning as described for Table 1.

Example 14

This example illustrates gelation in supercritical $CO_2$ ($scCO_2$).

A gelator was charged to a high-pressure variable volume view cell equipped with a TEFLON® polymer-coated stir bar and an electrical heating jacket. The cell was sealed and then charged with liquid CO2 to give a final gelator concentration of 0.3-0.7 wt %. The cell was then heated to about 70 to 100° C. and pressurized to about 260-350 bar (26.0-35.0 MPa) with agitation to solubilize a significant portion of the gelator. Agitation was then suspended and the cell was slowly cooled to room temperature over several hours at constant pressure to allow gel formation within the cell volume. The $CO_2$ was then slowly vented from the view cell, and the gelled sample was removed from the cell and imaged by scanning electron microscopy, revealing a gelled nanoweb microstructure. Table 3 summarizes the results for this series of examples.

TABLE 3

Summary for scCO₂ Gelation Examples

| Compound | Wt % gelator[†] | Temperature (° C.) | Pressure bar (MPa) |
|---|---|---|---|
| Compound 1 | 0.44 | 69 | 346 (34.6) |
| Compound 5 | 0.48 | 68 | 274 (27.4) |
| Compound 7 | 0.73 | 103 | 307 (30.7) |
| Compound 8 | 0.49 | 100 | 351 (35.1) |
| Compound 9 | 0.37 | 68 | 257 (25.7) |
| Compound 10 | 0.32 | 68 | 259 (25.9) |

[†]Overall gelator concentration in view cell. Actual $CO_2$ solubility was generally less than this concentration at the indicated conditions.

Example 15

Contact angle (CA) measurements to determine the contact angle of both water and hexadecane on a surface were performed using a Ramé-Hart Standard Automated Goniometer Model 200 employing DROP image standard software and equipped with an automated dispensing system with a 250 µl syringe and an illuminated specimen stage assembly; according to procedures in the Manufacturer's manual. The goniometer camera was connected through an interface to a computer that allowed the droplet to be visualized on a computer screen. The horizontal axis line and the cross line could both be independently adjusted on the computer screen using the software.

Prior to contact angle measurement, the sample was placed on the sample stage and the vertical vernier adjusted to align the horizontal line (axis) of the eye piece coincident to the horizontal plane of the sample, and the horizontal position of the stage relative to the eye piece positioned so as to view one side of the test fluid droplet interface region at the sample interface.

To determine the contact angle of the test fluid on the sample, approximately one drop of test fluid was dispensed onto the sample using a 30 µL pipette tip and an automated dispensing system to displace a calibrated amount of the test fluid. For water measurements deionized water was employed, and for oil measurements, hexadecane was suitably employed. Horizontal and cross lines were adjusted via the software in case of the Model 200 after leveling the sample via stage adjustment, and the computer calculated the contact angle based upon modeling the drop appearance. The initial contact angle is that angle determined immediately after dispensing the test fluid to the sample surface. Initial contact angles above 90 degrees are indicators of effective water and oil repellency. Contact angle can be measured after the droplet has been added to a surface (advancing contact angle, abbreviated "Adv CA") or after the droplet has been partially withdrawn from a surface (receding contact angle, abbreviated "Rec CA").

A 1 wt % solution of above compounds in a solvent (acetone, methanol or acetonitrile depending on the solubility) were dip-coated Mylar® PET film (Du Pont Teijin Films, Hopewell, Va. 23860). The films were then air or vacuum dried for 24 h before measuring the contact angles and the values are summarized in Table 4.

TABLE 4

Contact angle of dip-coated samples on MYLAR ® PET film

| | Contact angle[a,b] | | | |
|---|---|---|---|---|
| | Water | | Hexadecane | |
| Example | Adv CA | Rec CA | Adv CA | Rec CA |
| 1 | 114 ± 4 | 74 ± 3 | 77 ± 3 | 38 ± 2 |
| 2 | 88 ± 2 | 51 ± 3 | 62 ± 2 | 26 ± 2 |
| 3 | 87 ± 2 | 55 ± 2 | 59 ± 2 | 30 ± 1 |
| 4 | 101 ± 3 | 64 ± 2 | 62 ± 3 | 28 ± 2 |
| 5 | 110 ± 3 | 77 ± 1 | 71 ± 3 | 29 ± 2 |
| 6 | 95 ± 3 | 60 ± 1 | 62 ± 3 | 26 ± 4 |
| 7 | 117 ± 4 | 77 ± 4 | 74 ± 2 | 33 ± 3 |
| 8 | 93 ± 5 | 57 ± 3 | 54 ± 5 | 25 ± 3 |
| 9 | 111 ± 3 | 69 ± 1 | 80 ± 3 | 40 ± 1 |
| 10 | 87 ± 2 | 50 ± 3 | 58 ± 3 | 24 ± 2 |
| 11 | 109 ± 2 | 72 ± 2 | 71 ± 3 | 34 ± 2 |
| 12 | 91 ± 3 | 54 ± 2 | 57 ± 4 | 25 ± 3 |

[a]average of 3 runs at different positions on each sample,
[b]slight variations observed depending on the quality of the film prepared as well as the solvent used.

Example 16A and B

These examples illustrate the formation of composite materials from Compound 1 and porous supports: TYVEK® polyethylene nonwoven fabric; and KOLON® 70 gsm spunbound polyester fabric using Method 1—Gel-Impregnation on Nonwoven Supports.

By following the procedure for gel-impregnation on nonwoven supports, weighed samples of TYVEK® polyethylene nonwoven fabric (3.0 cm×3.0 cm) were gel-impregnated with a gel obtained by cooling a 1 wt % compound 1 in acetone; followed by drying the impregnated support under vacuum at RT; to provide a composite material 16A. The contact angle of the composite material and untreated TYVEK® fabric control were measured and the results summarized in Table 5. FIGS. 1A and B illustrate a scanning electron micrograph of composite material 16A at 2000× and 10,000× magnification. The larger fibers in FIG. 1A are the nonwoven support. The smaller fibers in FIG. 1B are representative of the nanoweb.

A similar composite material was prepared with KOLON® 70 gsm spunbound polyester fabric and Compound 1 to provide composite material 16B. The contact angle of the composite material and untreated KOLON® fabric control were measured and the results summarized in Table 5.

Example 17

Following the procedure as described in example 16, a weighed sample of KOLON® 70 gsm spunbound polyester fabric (3.0 cm×3.0 cm) was gel impregnated from a gel obtained by cooling a 2 wt % compound 5 in acetonitrile, followed by drying the impregnated support under vacuum at RT; to provide a composite material 17. The contact angle of the composite material was measured and the results are summarized in Table 5.

Example 18A and B

Following the procedure as described in example 16, a weighed sample of TYVEK® polyethylene nonwoven fabric (3.0 cm×3.0 cm) was gel impregnated from a gel obtained by cooling a 2 wt % Compound 7 in methanol, followed by drying the impregnated support under vacuum at RT, to provide a composite material 18A.

A similar composite material was prepared with KOLON® 70 gsm spunbound polyester fabric and compound 7 to provide composite material 18B.

The contact angles of the composite materials were measured and the results are summarized in Table 5.

Example 19A and B

Following the procedure as described in example 16, a weighed sample of TYVEK® polyethylene nonwoven fabric (3.0 cm×3.0 cm) was gel impregnated from a gel obtained by cooling a 2 wt % compound 8 in n-butanol, followed by drying the impregnated support under vacuum at RT; to provide a composite material 19A.

A similar composite material was prepared with KOLON® 70 gsm spunbound polyester fabric and compound 8 to provide composite material 19B.

The contact angles of the composite materials were measured and the results are summarized in Table 5. The results indicate that the composite materials exhibit significantly higher advancing contact angle with water than the untreated controls; and the composite materials exhibit high advancing contact angle with hexadecane; whereas the untreated controls rapidly absorb hexadecane.

TABLE 5

Contact angle of Controls and Composite Materials

| | Contact angle[a] | | | |
|---|---|---|---|---|
| | Water | | Hexadecane | |
| Example | Adv CA | Rec CA | Adv CA | Rec CA |
| TYVEK ® fabric | 108 ± 1 | 78 ± 1 | abs | abs |
| KOLON ® Fabric | 115 ± 4 | 85 ± 4 | abs | abs |
| 16A | 152 ± 5 | 122 ± 5 | 89 ± 4 | 50 ± 5 |
| 16B | 155 ± 2 | 132 ± 3 | 103 ± 4 | 54 ± 4 |
| 17 | 147 ± 1 | 46 ± 4 | 151 ± 1 | 62 ± 4 |
| 18A | 136 ± 4 | 100 ± 5 | 99 ± 3 | 53 ± 3 |
| 18B | 149 ± 4 | 106 ± 3 | 110 ± 4 | 58 ± 3 |
| 19A | 127 ± 3 | 84 ± 3 | 76 ± 4 | 42 ± 3 |
| 19B | 130 ± 4 | 110 ± 4 | 48 ± 3 | 16 ± 2 |

[a]average of 3 runs at different positions on each sample; abs = completely absorbed into fabric.

Example 20A and 20B

This example illustrates the gel impregnation of compound 8 in TYVEK® nonwoven polyethylene fabric and KOLON® 70 gsm spunbound polyester nonwoven fabrics in $scCO_2$ using Method 2-Gel-Impregnation on Nonwoven Supports in $scCO_2$.

A weighed sample of TYVEK® nonwoven fabric was mounted in a high-pressure variable volume view cell which had been charged with gelator compound 8. The cell was sealed and then charged with liquid $CO_2$ to give an overall gelator concentration of 1.0 wt %. The cell was then heated to 99° C. and pressurized to 306 bar (30.6 MPa) with agitation to solubilize a significant portion of the gelator. Agitation was then suspended and the cell was slowly cooled to room temperature over several hours at constant pressure to allow gel formation within and upon the TYVEK® nonwoven fabric. The $CO_2$ was then slowly vented from the view cell, and the resulting composite material 20A was removed, imaged by scanning electron microscopy, and utilized for contact angle measurements.

A composite material was prepared with KOLON® 70 gsm spunbound polyester fabric and Compound 8 using a similar procedure to provide composite material 20B.

The contact angles of the composite materials were measured, and the results are summarized in Table 6.

Example 21A and 21B

This example illustrates the gel impregnation of compound 9 in TYVEK® nonwoven fabric (21A) and KOLON® 70 gsm spunbound polyester (21B) nonwoven fabric in supercritical $CO_2$.

Following the procedure as described in example 20, a weighed sample of TYVEK® polyethylene nonwoven fabric was gel impregnated with Compound 9 at an overall gelator concentration of 0.33 wt %, temperature of 71° C., and cell pressure of 208 bar (20.8 MPa) to provide a composite material 21A.

A similar composite material was prepared with KOLON® 70 gsm spunbound polyester fabric and Compound 9 to provide composite material 21B.

The contact angles of the composite materials were measured, and the results are summarized in Table 6. A scanning electron micrograph at 2000× magnification of composite 21B was obtained, displayed in FIG. 2, and exhibited the nanoweb structure of the composite of the invention provided by gelation in scCO$_2$. The typical width of the fibers is about 0.1 to about 0.36 microns.

Example 22

This example illustrates the gel impregnation of compound 11 in KOLON® 70 gsm spunbound polyester nonwoven fabric in supercritical CO$_2$.

Following the procedure as described in example 20, a weighed sample of KOLON® 70 gsm spunbound polyester nonwoven fabric was gel impregnated with Compound 11 at an overall gelator concentration of 0.41 wt %, temperature of 68° C., and cell pressure of 310 bar (31.0 MPa) to provide a composite material 22. The contact angles of the composite material were measured, and the results are summarized in Table 6.

Example 23

This example illustrates the gel impregnation of compound 12 in KOLON® 70 gsm spunbound polyester nonwoven fabric in supercritical CO$_2$.

Following the procedure as described in example 20, a weighed sample of KOLON® 70 gsm spunbound polyester nonwoven fabric was gel impregnated with Compound 12 at an overall gelator concentration of 0.50 wt %, temperature of 68° C., and cell pressure of 355 bar (35.5 MPa) to provide a composite material 23. The contact angles of the composite material were measured, and the results are summarized in Table 6

TABLE 6

Contact angle of Composite Materials

| | Contact angle[a] | | | |
|---|---|---|---|---|
| | Water | | Hexadecane | |
| Example | Adv CA | Rec CA | Adv CA | Rec CA |
| 20A | 143 ± 4 | 122 ± 3 | 70 ± 1 | 28 ± 3 |
| 20B | 160 ± 2 | 141 ± 3 | 30 ± 5 | Abs |
| 21A | 147 ± 4 | 131 ± 3 | 66 ± 5 | 24 ± 4 |
| 21B | 157 ± 4 | 149 ± 2 | 94 ± 4 | 39 ± 4 |
| 22 | 159 ± 2 | 146 ± 2 | 81 ± 3 | 34 ± 3 |
| 23 | 154 ± 3 | 129 ± 3 | 68 ± 4 | 29 ± 3 |

[a]average of 3 runs at different positions on each sample.
Abs: slowly absorbed into fabric.

The results indicate that the composite materials of Examples 20-23 exhibit significantly higher advancing contact angle with water than the untreated controls; and the composite materials exhibit high advancing contact angle with hexadecane; whereas the untreated controls rapidly absorb hexadecane.

Example 24

This example illustrates the treatment of compound 7 on Granite and Limestone.

A 1 wt % solution of compound 7 in acetone was prepared by heating the mixture at 40° C. To this solution was immersed a weighed piece of clean Granite (about 5.0-5.0 cm squared) for 2 minutes (partial gel formation observed) and quickly removed. The granite piece was dried under vacuum at RT to provide a composite 24A, which was weighed and used for contact angle measurements.

A similar treatment of compound 7 was performed on a piece of clean Limestone (about 5.0-5.0 cm squared) to provide a composite 24B. The contact angles of the composite materials were measured and the results are compared with the untreated samples in Table 7.

Example 25

This example illustrates the treatment of compound 9 on Granite and Limestone.

Following the procedure as described in example 24, composites 25A and 25B were prepared from weighed samples of Granite (~5.0×5.0 cm squared) and Limestone (5.0×5.0 cm squared) using a 1 wt % solution of compound 9 in acetone. The contact angles of the composite materials were measured and the results are summarized in Table 7.

TABLE 7

| | Contact angle[a] | | | |
|---|---|---|---|---|
| | Water | | Hexadecane | |
| Example | Adv CA | Rec CA | Adv CA | Rec CA |
| Granite | 57 ± 4 | 17 ± 2 | 12 ± 2 | — |
| Limestone | 54 ± 3 | 9 ± 2 | 12 ± 1 | — |
| 24A | 145 ± 2 | 105 ± 3 | 76 ± 3 | 32 ± 3 |
| 24B | 158 ± 3 | 113 ± 4 | 71 ± 3 | 36 ± 3 |
| 25A | 118 ± 3 | 66 ± 2 | 90 ± 4 | 35 ± 2 |
| 25B | 159 ± 5 | 109 ± 4 | 86 ± 3 | 40 ± 1 |

[a]average of 3 runs at different positions on each sample

We claim:
1. A composition comprising super-critical carbon dioxide and a compound of formula (I)

$$R_o\text{-}[L\text{-}(C_qH_{2q}S)_pC_rH_{2r}R_f]_2 \qquad (I)$$

wherein
$R_o$ is a divalent organic group having 2 to 40 carbon atoms;
L is a linking group, —C(O)NH—, wherein the left side of the linking group is bonded to $R_o$;
p is an integer of 0 or 1;
q is an integer of 2 to 10;
r is an integer of 1 to 10; and
$R_f$ is a linear or branched $C_1$-$C_6$ perfluoroalkyl group.
2. The composition of claim 1 wherein $R_o$ is selected from the group $C_2$-$C_{18}$ linear or branched alkyl group; and $C_2$-$C_{18}$ linear or branched alkyl group substituted, or interrupted, by a $C_4$-$C_{16}$ cycloaliphatic group.
3. The composition of claim 1 wherein $R_o$ is —(CH$_2$)$_6$—.
4. The composition of claim 1 wherein $R_f$ is a linear or branched $C_3$-$C_6$ perfluoroalkyl group.
5. A composite material comprising a porous support and a porous nanoweb, wherein said porous nanoweb comprises fibrous structures of about 10 nm to about 1000 nm effective average fiber diameter as determined with electron microscopy; said fibrous structures comprising one or more compounds of formula (I):

$$R_o\text{-}[L\text{-}(C_qH_{2q}S)_pC_rH_{2r}R_f]_2 \qquad (I)$$

wherein
$R_o$ is a divalent organic group having 2 to 40 carbon atoms;
L is a linking group, —C(O)NH—, wherein the left side of the linking group is bonded to $R_o$;
p is an integer of 0 or 1;
q is an integer of 2 to 10;

r is an integer of 1 to 10; and $R_f$ is a linear or branched $C_1$-$C_6$ perfluoroalkyl group.

6. The composite material of claim 5 wherein $R_o$ is selected from the group $C_2$-$C_{18}$ linear or branched alkyl group; and $C_2$-$C_{18}$ linear or branched alkyl group substituted, or interrupted by, a $C_4$-$C_{16}$ cycloaliphatic group.

7. The composite material of claim 5, wherein $R_f$ is a linear or branched $C_3$-$C_6$ perfluoroalkyl group.

8. The composite material of claim 5, wherein the porous support is selected from woven fabrics comprising glass, polyamides, polyesters, and combinations thereof; and nonwoven fabrics comprising glass, paper, cellulose acetate and nitrate, polyamides, polyesters, polyolefins, and combinations thereof.

9. A solid substrate having disposed thereon a composition comprising the composition of claim 1.

10. The solid substrate of claim 9 selected from stone, masonry, concrete, unglazed tile, brick, porous clay, granite, limestone, grout, mortar, marble, wood, gypsum board, terrazzo, and composite materials.

11. A method for making a composite material comprising a porous support and a porous nanoweb comprising:
   (a) providing a porous support;
   (b) providing a gelling mixture comprising one or more solvents and one or more organogelator(s);
   (c) applying the gelling mixture to the porous support;
   (d) inducing said organogelator(s) to form a nanoweb gel; and
   (e) removing the solvent(s) from the nanoweb gel to provide a dry porous nanoweb coating on said porous support;

wherein said organogelator(s) is one or more compositions of formula (I):

$$R_o\text{-}[L\text{-}(C_qH_{2q}S)_pC_rH_{2r}R_f]_2 \quad (I)$$

wherein
  $R_o$ is a divalent organic group having 2 to 40 carbon atoms;
  L is a linking group, —C(O)NH—, wherein the left side of the linking group is bonded to $R_o$;
  p is an integer of 0 or 1;
  q is an integer of 2 to 10;
  r is an integer of 1 to 10; and
  $R_f$ is a linear or branched $C_1$-$C_6$ perfluoroalkyl group.

12. The method of claim 11, wherein $R_o$ is selected from the group $C_2$-$C_{18}$ linear or branched alkyl group; and $C_2$-$C_{18}$ linear or branched alkyl group substituted, or interrupted by, a $C_4$-$C_{16}$ cycloaliphatic group.

13. The method of claim 11, wherein $R_f$ is a linear or branched $C_3$-$C_6$ perfluoroalkyl group.

* * * * *